United States Patent
Peter et al.

(10) Patent No.: US 11,959,082 B2
(45) Date of Patent: Apr. 16, 2024

(54) DUAL ACTIVITY SUPER TOXIC RNAI ACTIVE DSRNAS

(71) Applicant: Northwestern University, Evanston, IL (US)

(72) Inventors: Marcus E. Peter, Chicago, IL (US); Andrea E. Murmann, Chicago, IL (US)

(73) Assignee: Northwestern University, Evanston, IL (US)

( * ) Notice: Subject to any disclaimer, the term of this patent is extended or adjusted under 35 U.S.C. 154(b) by 110 days.

(21) Appl. No.: 16/824,592

(22) Filed: Mar. 19, 2020

(65) Prior Publication Data

US 2020/0299697 A1    Sep. 24, 2020

Related U.S. Application Data

(60) Provisional application No. 62/821,782, filed on Mar. 21, 2019.

(51) Int. Cl.
*C12N 15/113* (2010.01)
*A61P 35/00* (2006.01)

(52) U.S. Cl.
CPC .......... *C12N 15/1135* (2013.01); *A61P 35/00* (2018.01); *C12N 2310/14* (2013.01)

(58) Field of Classification Search
CPC .. C12N 15/1135; C12N 2310/14; A61P 35/00
See application file for complete search history.

(56) References Cited

U.S. PATENT DOCUMENTS

| | | | |
|---|---|---|---|
| 4,458,066 A | 7/1984 | Caruthers | |
| 10,934,547 B2 | 3/2021 | Peter | |
| 2018/0251762 A1 | 9/2018 | Peter | |
| 2018/0320187 A1 | 11/2018 | Peter | |
| 2020/0299697 A1 | 9/2020 | Peter | |

FOREIGN PATENT DOCUMENTS

| | | |
|---|---|---|
| WO | 2018152523 A1 | 8/2018 |
| WO | 2018152524 A1 | 8/2018 |

OTHER PUBLICATIONS

Wei et al. (PLoS One (2009) 4(4): e5382). (Year: 2009).*
Bogerd HP, et al. (2014). Derivation and characterization of Dicer- and microRNA-deficient human cells. RNA. 20:923-37.
De Mezer M, et al. (2011). Mutant CAG repeats of Huntingtin transcript fold into hairpins, form nuclear foci and are targets for RNA interference. Nucleic Acids Res. 39:3852-63.
Eulalio A, et al. (2008). GW182 interaction with Argonaute is essential for miRNA-mediated translational repression and mRNA decay. Nat Struct Mol Biol. 15:346-53.
Foulkes WD, et al. (2014). Dicer1: mutations, microRNAs and mechanisms. Nat Rev Cancer. 14:662-72.
Gao, Q. Q., et al. "6mer seed toxicity in tumor suppressive microRNAs." Nature communications 9.1 (2018): 1-16.
Hammond, S.M. et al. "Post-transcriptional gene silencing by double-stranded RNA." Nature Reviews Genetics 2.2 (2001): 110-119.
Han J, et al. (2004). The Drosha-DGCR8 complex in primary microRNA processing. Genes Dev. 18:3016-27.
International Searching Authority. International Search Report and Written Opinion for application PCT/US2020/023717, dated Jul. 9, 2020.
Kumar MS, et al. (2007). Impaired microRNA processing enhances cellular transformation and tumorigenesis. Nat Genet. 39:673-7.
Kumar MS, et al. (2009). Dicer1 functions as a haploinsufficient tumor suppressor. Genes Dev. 23:2700-4.
Leuschner PJ, et al. (2006). Cleavage of the siRNA passenger strand during RISC assembly in human cells. EMBO Rep. 7:314-20.
Lewis BP, et al. (2003). Prediction of mammalian microRNA targets. Cell. 115:787-98.
Murmann AE, et al. "Small interfering RNA s based on huntingtin trinucleotide repeats are highly toxic to cancer cells." EMBO reports 19.3 (2018): e45336.
Murmann AE, et al. (2017). Induction of DISE in ovarian cancer cells in vivo. Oncotarget. 8:84643-58.
Murmann AE, et al. (2018). Trinucleotide repeat expansion diseases, RNAi and cancer. Trends in Cancer. 4:684-700.
Patel M, Peter ME. (2018). Identification of DISE-inducing shRNAs by monitoring cellular responses. Cell Cycle. 17:506-14.
Putzbach W, et al. (2017). Many si/shRNAs can kill cancer cells by targeting multiple survival genes through an off-target mechanism. eLife. 6: e29702.
Putzbach W, et al. (2018). CD95/Fas ligand mRNA is toxic to cells. eLife. 7:e38621.
Putzbach W, et al. (2018). DISE—A Seed Dependent RNAi Off-Target Effect that Kills Cancer Cells. Trends in Cancer. 4:10-9.
Swahari V, et al. (2016). Essential Function of Dicer in Resolving DNA Damage in the Rapidly Dividing Cells of the Developing and Malignant Cerebellum. Cell Rep. 14:216-24.

(Continued)

*Primary Examiner* — J. E. Angell
(74) *Attorney, Agent, or Firm* — Quarles & Brady LLP

(57) ABSTRACT

Disclosed are polynucleotides, compositions, and methods related to RNA interference (RNAi). Particular disclosed are toxic RNAi active seed sequences and methods of using toxic RNAi active sequences for killing cancer cells. The disclosed toxic RNAi active seed sequences preferentially target and inhibit the expression of multiple essential genes for cell survival and/or growth through a process called "death-induced by survival gene elimination" or "DISE." The disclosed toxic RNAi active seed sequences may be referred to as "dual activity super toxic RNAi active dsR-NAs" that include a toxic first strand and a toxic second strand that is complementary to the toxic first strand. As such, the disclosed dsRNAs may be expressed as shRNAs which are processed for RNA interference (RNAi) and either of the toxic first strand and the toxic second strand can function as a guide strand to initiate RNAi.

2 Claims, 7 Drawing Sheets
Specification includes a Sequence Listing.

(56) References Cited

OTHER PUBLICATIONS

Walton et al., "Designing highly active siRNAs for therapeutic applications," the FEBS Journal, 277 (2010) 4806-4813.
Wang Y, et al. (2008). Structure of the guide-strand-containing argonaute silencing complex. Nature. 456:209-13.

* cited by examiner

B

GGGUGG GCUAAC GGAGGU GGGGGU GGUGGU GGUGCU GGUGGA
GGGCGG GGCUGG GGGGGC GGGUGC GGGGGA GGUGCC GUCCUC GAUGCC
GGGCAG GGGUGA GGCGGG GCUAGU GGGCUG GGGGCA CGGGGG GGGGCC
GCAGGC GGGGCG GUGGGU GGGAGU CCAUGG GGGGUG GGGGCG GGCUCU
GGGAUC GAAGUC GCUGGG GCAGGU CGGGGC GGAGGA GCUAAU GAGGGC
GGUGGC GCGGGC GGAGCC GGCAGG GGCGGGU AGUAGC GACAUC CGGGUC
GACUGC AGCUGG GUGGGC GGGCCU CUGGGC GGUGAC UGGCGG GGGCCG
GGGCGU GCGGGG GGGCGC GGGGGG CGUAGC UCGGGC GGAGGG GCGGGCG
GUCUGG GGGCAA GGGGGA GCCUGU CGCCGC GUUGCC GAUACC UGGUGG
GGGUAG CGGGCC UAUGCC GGGAGG GGCAGC CCUGGG UGCCUG ACAGGC
GAUGGC CGGUGG GGCCGG UGGGGG GUGGGG GACAGC GGGAGA GGGUGU
CAGGCC GAUGCU GUAGCU AACCCC GAGACU GGGGAG GGCACC GGUUGG
CGUUGC AGGAGC GCGGGU GGGCAU GGUGCG GCCAUC GUAGCU CGGCUC
GGGAGG UAUCCC GCAGGG CGCGGC GGGCCA GAGGGU AGUAGU GCCUGC
CGGGGU GGCGGC GUCUCC GCCUC GGAUGC GGGUCU GGAGGC GCGGGUC
CAUGCC CCUGGC GGAGCU CCAGCC AUUGCC GGCUAC GGCUGC AGGUGC
GGGAGC AGGGGC CUGGGA GUUGCU GUCUGG CAUGCU GUAGCU CGGCUC
UGUAGU UCGUGC AGUUCC GCCGGU GCUCUC GCUACU GGGGUC GCGGCU
GGGAGG GGGCUC CGCAGG GGCUC GUUGGG UGGGCU UGGGAG GCUGCC AGGAC
GACGGC AGGGGG CUUGGA GAGGGG GCCUUC CGGAGG CGGGCGG CAGGGC
GGCCGC AGGGCU GAAGAU GACUCC UAUGCU ACACCU GAAGGC CCGUGC
GGCGCC CUGGGG GCGUUC AGUUGC GGCAUC GAGGAC GCGGGA GCGCUC
GGGUCC CGUGGC GGUUGC GGGCUA CUUGGG ACCCCC AGGUCU UGCAAC
ACAUGC GCGAGU GGCCUC GGCUAU CGGUGC UACACC CGGAGC AGCGGC
GGUCCU CUUGCC GCGGCA CGGCGC GGCCGU GAGGCC GGCGAC GUUCCA

DUAL ACTIVITY SUPER TOXIC RNAI ACTIVE DSRNAS

CROSS-REFERENCE TO RELATED APPLICATIONS

This Application claims the benefit of U.S. Provisional Application No. 62/821,782, filed Mar. 21, 2019, the content of which is incorporated herein by reference in its entirety.

STATEMENT REGARDING FEDERALLY SPONSORED RESEARCH OR DEVELOPMENT

This invention was made with government support under CA197450 awarded by the National Institutes of Health. The government has certain rights in the invention.

SEQUENCE LISTING

A Sequence Listing accompanies this application and is submitted as an ASCII text file of the sequence listing named "702581.01721_Sequence_Listing_New_ST25.txt" which is 10,510 bytes in size and was created on Jan. 22, 2024. The sequence listing is electronically submitted via Patent Center and is incorporated herein by reference in its entirety.

BACKGROUND

The field of the invention relates to RNA interference (RNAi) and the use of RNAi active sequences for treating diseases and disorders. In particular, the field of the invention relates to the use of dual activity toxic RNAi active seed sequences for killing cancer cells.

SUMMARY

Disclosed are polynucleotides, compositions, and methods related to RNA interference (RNAi). The disclosed polynucleotides, compositions, and methods may be utilized for treating diseases and disorders through RNAi. Particular disclosed are toxic RNAi active seed sequences and methods of using toxic RNAi active seed sequences for killing cancer cells.

The disclosed toxic RNAi active seed sequences preferentially target and inhibit the expression of multiple essential genes for cell survival and/or growth through a process called "death-induced by survival gene elimination" or "DISE." The disclosed toxic RNAi active seed may be presented or administered in siRNAs, shRNAs, and/or vectors that express siRNAs and/or shRNAs such as viral vectors (e.g., adenovirus-associated virus vectors and lentiviral vectors).

The disclosed toxic RNAi active seed sequences may be referred to as "dual activity super toxic RNAi active dsRNAs." The disclosed dsRNAs are "dual active" in that the dsRNAs include a toxic first strand and a toxic second strand that is complementary to the toxic first strand. As such, the disclosed dsRNAs may be expressed as shRNAs which are processed for RNA interference (RNAi) and either of the toxic first strand and the toxic second strand can function as a guide strand to initiate RNAi.

DETAILED DESCRIPTION

Figure 1:
FIG. 1: The high toxicity consensus and the 200 most toxic 6mer seeds. (A) Average contribution of the four nucleotides to each of the 6 positions in the 6mer seed sequences in the 200 siRNAs that were found to be most toxic to two human cell lines (HeyA8 and H460) (22). (B) The 200 6mer seed sequences that were found to be most toxic to the two human cell lines.

The present invention is described herein using several definitions, as set forth below and throughout the application.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

Unless otherwise specified or indicated by context, the terms "a", "an", and "the" should be interpreted to mean "one or more." For example, "an shRNA" or "an siRNA" should be interpreted to mean "one or more shRNA's" and "one or more siRNA's," respectively As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" should be interpreted to mean plus or minus ≤10% of the particular term and "substantially" and "significantly" should be interpreted to mean plus or minus >10% of the particular term.

As used herein, the terms "include" and "including" should be interpreted to have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject" may be interchangeable with "patient" or "individual" and means an animal, which may be a human or non-human animal, in need of treatment.

A "subject in need of treatment" may include a subject having a disease, disorder, or condition that can be treated by administering to the subject one or more therapeutic RNAs as disclosed herein. A subject in need thereof may include a subject having or at risk for developing a cell proliferative disease or disorder such as cancer. A subject in need thereof may include, but is not limited to, a subject having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus). As such, methods of treating cancers are contemplated herein, including methods of treating cancers selected from, but not limited to any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus).

As used herein, a "toxic RNA" refers to an RNA molecule that induces cell death via RNA interference (RNAi) when the RNA molecule is expressed in a cell. Toxic RNAs may include, but are not limited to toxic shRNA, toxic siRNA (which may have been processed via Dicer from a corresponding shRNA), toxic pre-miRNA which may artificial or engineered pre-miRNA, and/or toxic miRNA (which may have been processed via Dicer from a corresponding pre-miRNA). Toxic RNAs have been disclosed in the art. (See U.S. Published Application Nos. 20180251762 and 20180320187, the contents of which are incorporated herein by reference in their entireties).

As used herein, the terms "silencing" and "inhibiting the expression of" refer to at least partial suppression of the expression of a target gene, for example, as manifested by a reduction of mRNA associated with the target gene.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "pharmaceutical composition" may include be defined as a composition that includes a pharmacologically effective amount of a toxic RNA and/or extracellular particles comprising the toxic RNA and a pharmaceutically acceptable carrier for delivering the toxic RNA to target cells or target tissue. As used herein, the term "pharmaceutically acceptable carrier" refers to a carrier for administration of a therapeutic agent which facilitates the delivery of the therapeutic agent (e.g., a toxic RNA and/or extracellular particles comprising the toxic RNA) to target cells or target tissue. As used herein, the term "therapeutically effective amount" refers to that amount of a therapeutic agent that provides a therapeutic benefit in the treatment, prevention, or management of a disease or disorder (e.g., a cell proliferation disease or disorder such as cancer).

Polynucleotides

The disclosed technology relates to nucleic acid and the use of nucleic acid for treating diseases and disorders. The terms "nucleic acid" and "oligonucleotide," as used herein, refer to polydeoxyribonucleotides (containing 2-deoxy-ribose), polyribonucleotides (containing ribose), and to any other type of polynucleotide that is an N glycoside of a purine or pyrimidine base. As used herein, the terms "A," "T," "C", "G" and "U" refer to adenine, thymine, cytosine, guanine, uracil as a nucleotide base, respectively. There is no intended distinction in length between the terms "nucleic acid," "oligonucleotide," and "polynucleotide," and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

The disclosed polynucleotides may include a fragment of a reference polynucleotide. As used herein, a "fragment" of a polynucleotide is a portion of a polynucleotide sequence which is identical in sequence to but shorter in length than a reference sequence. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide; in other embodiments a fragment may comprise no more than 5, 10, 15, 20, 25, 30, 40, 50, 60, 70, 80, 90, 100, 150, 250, or 500 contiguous nucleotides of a reference polynucleotide; in further embodiments a fragment may comprise a range of contiguous nucleotides of a reference polynucleotide bounded by any of the foregoing values (e.g. a fragment comprising 20-50 contiguous nucleotides of a reference polynucleotide). Fragments may be preferentially selected from certain regions of a molecule. The term "at least a fragment" encompasses the full length polynucleotide. A "variant," "mutant," or "derivative" of a reference polynucleotide sequence may include a fragment of the reference polynucleotide sequence.

The disclosed polynucleotides may include a deletion relative to a reference polynucleotide. As used herein, a "deletion" refers to a change in a reference nucleotide sequence that results in the absence of one or more nucleotide residues. For example, a deletion may remove at least 1, 2, 3, 4, 5, 10, 20, 50, 100, or 200 nucleotide residues or a range of nucleotide residues bounded by any of these values (e.g., a deletion of 5-10 nucleotides). A deletion may include an internal deletion or a terminal deletion (e.g., an 5'-terminal truncation or a 3'-terminal truncation of a reference polynucleotide). A "variant" of a reference nucleotide sequence may include a deletion relative to the reference polynucleotide sequence.

The disclosed polynucleotides may include an insertion or an addition relative to a reference polynucleotide. As used herein, "insertion" and "addition" refer to changes in an nucleotide sequence resulting in the addition of one or more nucleotide residues. An insertion or addition may refer to 1, 2, 3, 4, 5, 10, 20, 30, 40, 50, 60, 70, 80, 90, 100, 150, or 200 nucleotide residues or a range of nucleotide residues bounded by any of these values (e.g., an insertion or addition of 5-10 nucleotides). A "variant" of a reference polynucleotide sequence may include an insertion or addition relative to the reference polynucleotide sequence.

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "promoter" as used herein refers to a cis-acting DNA sequence that directs RNA polymerase and other trans-acting transcription factors to initiate RNA transcription from the DNA template that includes the cis-acting DNA sequence. Promoters may include inducible promoter, which are promoters that can be induced to function in the presence of an effector molecule as known in the art.

As used herein, the term "complementary" in reference to a first polynucleotide sequence and a second polynucleotide sequence means that the first polynucleotide sequence will base-pair exactly with the second polynucleotide sequence throughout a stretch of nucleotides without mismatch. The term "cognate" may in reference to a first polynucleotide sequence and a second polynucleotide sequence means that the first polynucleotide sequence will base-pair with the second polynucleotide sequence throughout a stretch of nucleotides but may include one or more mismatches within the stretch of nucleotides. As used herein, the term "complementary" may refer to the ability of a first polynucleotide to hybridize with a second polynucleotide due to base-pair interactions between the nucleotide pairs of the first polynucleotide and the second polynucleotide (e.g., A:T, A:U, C:G, G:C, G:U, T:A, U:A, and U:G).

As used herein, the term "complementarity" may refer to a sequence region on an anti-sense strand that is substantially complementary to a target sequence but not fully complementary to a target sequence. Where the anti-sense strand is not fully complementary to the target sequence, mismatches may be optionally present in the terminal regions of the anti-sense strand or elsewhere in the anti-sense strand. If mismatches are present, optionally the mismatches may be present in terminal region or regions of the anti-sense strand (e.g., within 6, 5, 4, 3, or 2 nucleotides of the 5' and/or 3' terminus of the anti-sense strand).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions." Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem.

and Mol. Biol. 26(3/4):227-259; and Owczarzy et al., 2008, Biochemistry, 47: 5336-5353, which are incorporated herein by reference).

As used herein, the term "double-stranded RNA" ("dsRNA") refers to a complex of ribonucleic acid molecules having a duplex structure comprising two anti-parallel and substantially complementary nucleic acid strands.

As used herein, the term "nucleotide overhang" refers to an unpaired nucleotide or nucleotides that extend from the 5'-end or 3'-end of a duplex structure of a dsRNA when a 5'-end of one strand of the dsRNA extends beyond the 3'-end of the other strand, or when a 3'-end of one strand of the dsRNA extends beyond the 5'-end of the other strand. A nucleotide overhang may include ribonucleotides and/or deoxyribonucleotide (e.g., dAdA or TT).

As used herein, the term "blunt" refers to a dsRNA in which there are no unpaired nucleotides at the 5'-end and/or the 3'-end of the dsRNA (i.e., no nucleotide overhang at the 5'-end or the 3'-end). A "blunt ended" dsRNA is a dsRNA that has no nucleotide overhang at the 5'-end or the 3'-end of the dsRNA molecule.

As used herein, the term "anti-sense strand" refers to a strand of a dsRNA which includes a region that is substantially complementary to a target sequence (i.e., where the target sequence has a sequence corresponding to the sense strand).

As used herein, the term "sense strand," refers to the strand of a dsRNA that includes a region that is substantially complementary to a region of the anti-sense strand and that includes a region that substantially corresponds to a region of the target sequence.

As used herein, RNAi active sequences may include "siRNA" and "shRNA" and dsRNA that is processed by nucleases to provide siRNA and/or shRNA. The term "siRNA" refers to a "small interfering RNA" and the term "shRNA" refers to "short hairpin RNA." RNA interference (RNAi) refers to the process of sequence-specific post-transcriptional gene silencing in a cell or an animal mediated by siRNA and/or shRNA.

As used herein, the term "siRNA targeted against mRNA" refers to siRNA specifically promote degradation of the targeted mRNA via sequence-specific complementary multiple base pairings (e.g., at least 6 contiguous base-pairs between the siRNA and the target mRNA at optionally at least 7, 8, 9, 10, 11, 12, 13, 14, 15, 16, 17, 18, 19, 20, 21, 22, or 23 contiguous base-pairs between the siRNA and the target mRNA).

As used herein, RNAi active sequences may include "pre-miRNA" and "miRNA" and dsRNA that is processed to provide pre-miRNA and miRNA. The term "pre-miRNA" refers to a "pre-micro RNA" and the term "miRNA" refers to "micro RNA." RNA interference (RNAi) refers to the process of sequence-specific post-transcriptional gene silencing in a cell or an animal mediated by pre-miRNA and/or miRNA.

The terms "target, "target sequence", "target region", and "target nucleic acid," as used herein, are synonymous and refer to a region or sequence of a nucleic acid which may be selected as a sequence to which the anti-sense strand of siRNA or shRNA is substantially complementary to and hybridizes to as discussed herein. A target sequence may refer to a contiguous portion of a nucleotide sequence of an mRNA molecule of a particular gene, including but not limited to, genes that are essential for survival and/or growth of cells and in particular cancer cells. The target sequence of a siRNA refers to a mRNA sequence of a gene that is targeted by the siRNA due to complementarity between the anti-sense strand of the siRNA and the mRNA sequence and to which the anti-sense strand of the siRNA hybridizes when brought into contact with the mRNA sequence.

As used herein, the term "transfecting" means "introducing into a cell" a molecule, which may include a polynucleotide molecule such as dsRNA. When referring to a dsRNA, transfecting means facilitating uptake or absorption into the cell, as is understood by the skilled person. Absorption or uptake of dsRNA can occur or may be facilitated through passive diffusive or active cellular processes, or through the use of auxiliary agents or devices. Transfection into a cell includes methods known in the art such as electroporation and lipofection. However, the meaning of the term "transfection" is not limited to introducing molecules into cells in vitro. As contemplated herein, a dsRNA also may be "introduced into a cell," where the cell is part of a living organism. For example, for in vivo delivery, a dsRNA may be injected into a tissue site or may be administered systemically.

RNA Interference

The mechanism of action of RNA interference (RNAi) is understood by the skilled person. Interfering RNA (RNAi) generally refers to process that utilizes a single-stranded RNA (ssRNA) or double-stranded RNA (dsRNA) to inhibit expression of a target. The dsRNA is capable of targeting specific messenger RNA (mRNA) and silencing (i.e., inhibiting) the expression of a target gene. During this process, dsRNA (which may include shRNA or pre-miRNA) is enzymatically processed into short-interfering RNA (siRNA) duplexes or miRNA duplexes by a nuclease called Dicer. The anti-sense strand of the siRNA duplex or miRNA duplex (referred to as the "guide strand") is then incorporated into a cytoplasmic complex of proteins (RNA-induced silencing complex or RISC). The sense strand of the siRNA duplex of miRNA duplex (referred to as the "passenger strand") is degraded. The RISC complex containing the anti-sense siRNA strand or anti-sense miRNA strand binds mRNA which has a sequence complementary to the anti-sense strand-allowing complementary base-pairing between the anti-sense strand and the sense mRNA molecule. The mRNA molecule is then specifically cleaved by an enzyme (RNase) associated with RISC called Argonaut 2 (Ago2) resulting in specific gene silencing. For gene silencing or knock down (i.e., mRNA cleavage) to occur, anti-sense RNA has to become incorporated into the RISC. This represents an efficient process that occurs in nucleated cells during regulation of gene expression.

In particular, siRNA-mediated RNA interference may be considered to involve two-steps: (i) an initiation step, and (ii) an effector step. In the first step, input siRNA is processed into small fragments by Dicer. These small fragments are ~21-23-nucleotide in length and are called "guide RNAs." The guide RNAs can be incorporated into the protein-RNA RISC complex which is capable of degrading mRNA. As such, the RISC complex acts in the second effector step to destroy mRNAs that are recognized by the guide RNAs through base-pairing interactions via Ago2. RNA interference may be considered to involve the introduction by any means of double stranded RNA into a cell which triggers events that cause the degradation of a target RNA, and as such may be considered to be a form of post-transcriptional gene silencing. The skilled person understands how to prepare and utilize RNA molecules in RNAi. (See, e.g., Hammond et al., Nature Rev Gen 2: 110-119 (2001); and Sharp, Genes Dev 15: 485-490 (2001), the contents of which are incorporate herein by reference in their entireties).

In one aspect, the present inventors have disclosed toxic RNAs that silence expression of one or more mRNA's of essential genes that are required for survival and growth of cells such as cancer cells. Preferably, the disclosed toxic RNA molecules silence the expression of multiple mRNA's of essential genes that are required for survival and growth of cells such as cancer cells through a process similar to the process called "death-induced by survival gene elimination" or "DISE." Because in RNAi only a single strand of the siRNA duplex of miRNA duplex functions in RNAi, a cancer cell could evolve resistance to the inventors' toxic RNAs by evolving mechanisms in which the non-toxic strand of the siRNA duplex of miRNA duplex is selected for RNAi rather than the toxic strand. As such, the inventors here disclose dual activity toxic dsRNAs, which may be referred to as "dual activity super toxic RNAi active dsR-NAs." The disclosed dsRNAs are "dual active" in that the dsRNAs include a toxic first strand and a toxic second strand that is complementary to the toxic first strand. As such, the disclosed dsRNAs may be expressed as shRNAs which are processed for RNA interference (RNAi) and either of the toxic first strand and the toxic second strand can function as a guide strand to initiate RNAi.

For purposes of this application, the anti-sense strand of the siRNA may comprise a contiguous nucleotide sequence, where the base sequence of the anti-sense strand has substantial or complete sequence complementarity to the base sequence of a contiguous nucleotide sequence of corresponding length contained in an mRNA sequence of the targeted mRNA (e.g., in a non-coding 3'-end of an mRNA sequence). Substantial complementary permits some nucleotide mismatches (i.e., non-pairing nucleotides) and as such, the anti-sense strand of the siRNA need not have full complementarity.

In some embodiments, at least a portion of an anti-sense strand of an siRNA molecule comprises or consists of a sequence that is 100% complementary to a target sequence or a portion thereof. In another embodiment, at least a portion of an anti-sense strand of an siRNA molecule comprises or consists of a sequence that is at least about 90%, 95%, or 99% complementary to a target sequence or a portion thereof. For purposes of this application, the anti-sense strand of the siRNA molecule preferably comprises or consists of a sequence that specifically hybridizes to a target sequence or a portion thereof so as to inhibit expression of the target mRNA. The portion of the anti-sense strand of an siRNA molecule that comprises or consists of a sequence that is 100% complementary to a target sequence or a portion thereof may be a 6-nucleotide sequence referred to as a "seed sequence" which may be complementary to a corresponding 6-nucleotide sequence in a 3' UTR of a mRNA of a survival gene. The complementarity in this 6-nucleotide seed sequence may be sufficient to induce "death-induced by survival gene elimination" or "DISE" as disclosed herein.

Methods for preparing and isolating siRNA also are known in the art. (See, e.g., Sambrook et al., Molecular Cloning, A Laboratory Manual (2.sup.nd Ed., 1989), the content of which is incorporated herein by reference in its entirety). The disclosed siRNA may be chemically synthesized, using any of a variety of techniques known in the art. The disclosed siRNA may include modifications, for example, modifications that stabilize the siRNA and/or protect the siRNA from degradation via endonucleases and/or exonucleases. In some embodiments, the disclosed siRNA may include nucleic acid protecting and coupling groups, such as dimethoxytrityl at the 5'-end and/or phosphoramidites at the 3'-end.

In one embodiment, the disclosed dsRNAs comprise a double stranded region of about 15 to about 30 nucleotides in length. Preferably, the disclosed RNAs are about 20-25 nucleotides in length. The disclosed RNAs of the present invention are capable of silencing the expression of a target sequence in vitro and in vivo.

In one embodiment, the dsRNA disclosed herein comprises a hairpin loop structure and may be referred to as shRNA which may be processed to a siRNA. In another embodiment, the dsRNA or siRNA has an overhang on its 3' or 5' ends relative to the target RNA which is to be cleaved. The overhang may be 2-10 nucleotides long. In one embodiment, the dsRNA or siRNA does not have an overhang (i.e., the dsRNA or siRNA has blunt ends).

In another embodiment, the disclosed dsRNA molecules (e.g., siRNA molecules) may contain one or more modified nucleotides, including one or more modified nucleotides at the 5' and/or 3' terminus of the RNA molecules. In yet another embodiment, the disclosed RNA molecules may comprise one, two, three four or more modified nucleotides in the double-stranded region. Exemplary modified nucleotides may include but are not limited to, modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and the like. The preparation of modified siRNA is known by one skilled in the art. In some embodiments, the disclosed dsRNA molecules include one or more modified nucleotides at the 5'-terminus of the passenger strand of the dsRNA that prevent incorporation of the passenger strand into RISC. (See, e.g., Walton et al., Minireview: "Designing highly active siRNAs for therapeutic applications," the FEBS Journal, 277 (2010) 4806-4813).

In some embodiments, the disclosed siRNA molecules are capable of silencing one or more target mRNAs and may reduce expression of the one or more target mRNAs by at least about 20%, 30%, 40%, 50%, 60%, 70%, 80%, 90%, or 100% relative to a control siRNA molecule (e.g., a molecule not exhibiting substantial complementarity with the target mRNA). As such, in some embodiments, the presently disclosed siRNA molecules targeting the mRNA of essential genes may be used to down-regulate or inhibit the expression of essential genes (e.g., by at least about 20%, 30%, 40%, 50%, 60%, 70%, 80%, 90%, or 100% relative to a control siRNA molecule).

The disclosed dsRNA molecules may conveniently be delivered to a target cell or a target tissue through a number of delivery systems. For example, RNA may be delivered via electroporation, lipofection, calcium phosphate precipitation, plasmids, viral vectors that express the RNA, viral nucleic acids, phage nucleic acids, phages, cosmids, nanoparticles, or via transfer of genetic material in cells or carriers such as cationic liposomes. In one embodiment, transfection of RNA may employ viral vectors, chemical transfectants, or physico-mechanical methods such as electroporation and direct diffusion of DNA.

Dual Activity Super Toxic RNAi Active dsRNAs

The disclosed technology relates to toxic RNA that is active in RNA interference (RNAi). In particular, the disclosed technology relates to dual activity dsRNAs.

In some embodiments, the disclosed polynucleotides comprise a dsRNA sequence having a first strand, otherwise referred to as an "A" strand, and a second strand, otherwise referred to as a "B" strand, the dsRNA defined as follows:

```
5'-A01 A02 A03 A04 A05 A06 A07 A08 A09 A10 A11 A12 A13 A14 A15 A16 A17 A18 A19 A20 A21-3'
    |   |   |   |   |   |   |   |   |   |   |   |   |   |   |   |   |   |   |   |   |
3'-B21 B20 B19 B18 B17 B16 B15 B14 B13 B12 B11 B10 B09 B08 B07 B06 B05 B04 B03 B02 B01-5'
``` wherein:

A01 through A21 and B01 through B21 are any ribonucleotide selected from A, U, G, and C, provided that:

A01-A21 are complementary to B01-B21;

A01 and B01 are A or U;

the percentage GC content of the region from A02-A07 (B15-B20) is 66-100%;

the percentage of GC content of the region from A08-A14 (B08-B14) is 0-33%; and (v) the percentage GC content of the region from A15-A19 (B02-B07) is 66-100%.

In other embodiments, the disclosed polynucleotides comprise a dsRNA sequence having a first strand, otherwise referred to as an "A" strand, and a second strand, otherwise referred to as a "B" strand, the dsRNA defined as follows:

```
5'-A01 A02 A03 A04 A05 A06 A07 A08 A09 A10 A11 A12 A13 A14 A15 A16 A17 A18 A19 A20 A21-3'
    |   |   |   |   |   |   |   |   |   |   |   |   |   |   |   |   |   |   |   |   |
3'-B21 B20 B19 B18 B17 B16 B15 B14 B13 B12 B11 B10 B09 B08 B07 B06 B05 B04 B03 B02 B01-5'
``` wherein:

A01 through A21 and B01 through B21 are any ribonucleotide selected from A, U, G, and C, provided that:

A01-A21 are complementary to B01-B21, respectively;

A01 and B01 are A or U;

the percentage GC content of the region in the A strand from A02-A07 is 66-100%, and the B strand comprises a trinucleotide repeat sequence $(X_1X_2X_3)_n$, wherein $X_1$, $X_2$, and $X_3$ independently are selected from any ribonucleotide A, C, G, and U, and n is an integer from 3-10; or the percentage GC content of the region in the B strand from B02-B07 is 66-100%, and the A strand comprises a trinucleotide repeat sequence $(X_1X_2X_3)_n$, wherein $X_1$, $X_2$, and $X_3$ independently are selected from any ribonucleotide A, C, G, and U, and n is an integer from 3-10

In some embodiments of the disclosed polynucleotides, A02-A07 and B02-B07 comprise the sequence GGNNNN and N is any nucleotide. Optionally, at least one of A02-A07 and B02-B07 comprise the sequence GGGGGC.

In some embodiments of the disclosed polynucleotides, A02-A07 and B02-B07 comprise the sequence NNNNNN, which is a polynucleotide sequence present in the 3' UTR of an mRNA for an oncogene or a survival/housekeeping gene. Preferably, at least one of the A strand and the B strand downregulates expression of one or more survival genes when the polynucleotide is transfected or expressed in a cell.

In some embodiments of the disclosed polynucleotides, the contiguous sequence of A02-A07 and B02-B07 are independently selected from the group consisting of GGGCAG, GGGGCU, GGGCUG, GGGCGA, GGGGGC, GGGGGU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGC, GGCAUC, GCUGCU, CGGUGG, GUGUUC, GUCCAC, GGGCU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, CGGCUC, UCGUGC, GUUCCU, and GUCUGU.

In some of the disclosed polynucleotides having a trinucleotide repeat, the trinucleotide repeat sequence has a GC content of at least 33% or the trinucleotide repeat sequence has a GC content of at least 66%. In further embodiments of the disclosed polynucleotides having a trinucleotide repeat, the trinucleotide repeat sequence may be selected from the group consisting of $(ACC)_n$, $(ACG)_n$, $(AGC)_n$, $(AGG)_n$, $(CAC)_n$, $(CAG)_n$, $(CCA)_n$, $(CCC)_n$, $(CCG)_n$, $(CCU)_n$, $(CGA)_n$, $(CGC)_n$, $(CGG)_n$, $(CGU)_n$, $(CUC)_n$, $(CUG)_n$, $(GAC)_n$, $(GAG)_n$, $(GCA)_n$, $(GCC)_n$, $(GCG)_n$, $(GCU)_n$, $(GGA)_n$, $(GGC)_n$, $(GGG)_n$, $(GGU)_n$, $(GUC)_n$, $(GUG)_n$, $(UCC)_n$, $(UCG)_n$, $(UGC)_n$, and $(UGG)_n$. Optionally, the trinucleotide repeat sequence is $(CAG)_n$ or $(CUG)_n$.

In some embodiments of the disclosed polynucleotides at least one of the A strand and the B strand further comprises a 3' overhang comprising deoxyribonucleotides. Optionally, at least one of the A strand and the B strand further comprises a 3' overhang which comprises dAdA or TT.

In some embodiments, the disclosed polynucleotides comprising a dsRNA sequence may be present as part of a siRNA. In other embodiments, the disclosed polynucleotides comprising a dsRNA sequence may be present as part of a shRNA, for example, wherein the 3' of the A strand is linked via polynucleotides to the 5' end of the B strand and/or wherein the 3' end of the B strand is linked via polynucleotides to the 5' end of the A strand, and the linking polynucleotide for a loop. The shRNA comprising the dsRNA sequence may be processed via Dicer to prepare an RNAi active siRNA.

In some embodiments, the disclosed polynucleotides are expressed via an expression vector which optionally is inducible. For example, the disclosed polynucleotides may include shRNA that is expressed via an expression vector.

In some embodiments, the disclosed expression vectors may be present in a cell such as a eukaryotic cell. In some embodiments, the disclosed expression vectors express a dual activity toxic shRNA and are present in a eukaryotic cell which has been engineered to be deficient in a gene that is required for processing toxic shRNA to siRNA for RNA interference (RNAi). As such, the eukaryotic cell can be utilized to express the dual activity toxic shRNA and the eukaryotic cell will be resistant to the toxicity of the shRNA.

In some embodiments, the disclosed polynucleotides and expression vectors may be formulated as pharmaceutical compositions comprising the polynucleotides and/or expression vectors and optionally comprising a pharmaceutically acceptable carrier, excipient, or diluent.

Also disclosed herein are extracellular vesicles comprising the disclosed polynucleotides. In some embodiments, the disclosed extracellular vesicles may be produced and isolated from a eukaryotic cell that expresses the disclosed polynucleotides. For example, a eukaryotic cell which has been engineered to be deficient in a gene that is required for processing toxic shRNA to siRNA for RNA interference (RNAi) can be utilized to produce dual activity toxic shRNA as contemplated herein as well as extracellular vesicles (e.g. exosomes) that comprise the dual activity toxic shRNA as contemplated herein. The extracellular vesicles may be formulated as a pharmaceutical composition comprising the extracellular vesicles and optionally a pharmaceutically acceptable carrier, excipient, or diluent.

The disclosed polynucleotides, expression vectors, extracellular vesicles, and pharmaceutical compositions comprising the same may be administered in methods for treating a disease or disorder in a subject in need thereof. In some embodiments of the disclosed methods, the disease or disorder is a cell proliferative disease or disorder such as cancer. In particular, the disclosed polynucleotides, expression vectors, extracellular vesicles, and pharmaceutical compositions comprising the same may be administered to inhibit the growth of a cancer cell or to kill a cancer cell.

Illustrative Embodiments

The embodiments described below are illustrative of the methods, compositions, and systems disclosed herein and are not intended to be limiting.

1. A first illustrative embodiment includes a polynucleotide comprising a dsRNA sequence having a first strand, otherwise referred to as an "A" strand, and a second strand, otherwise referred to as a "B" strand, the dsRNA defined as follows:

```
5'-A01 A02 A03 A04 A05 A06 A07 A08 A09 A10 A11 A12 A13 A14 A15 A16 A17 A18 A19 A20 A21-3'
    |   |   |   |   |   |   |   |   |   |   |   |   |   |   |   |   |   |   |   |   |
3'-B21 B20 B19 B18 B17 B16 B15 B14 B13 B12 B11 B10 B09 B08 B07 B06 B05 B04 B03 B02 B01-5'
``` wherein:
A01 through A21 and B01 through B21 are any ribonucleotide selected from A, U, G, and C, provided that:
A01-A21 are complementary to B01-B21;
A01 and B01 are A or U;
the percentage GC content of the region from A02-A07 (B15-B20) is 66-100%;
the percentage of GC content of the region from A08-A14 (B08-B14) is 0-33%; and
(v) the percentage GC content of the region from A15-A19 (B02-B07) is 66-100%.

2. The polynucleotide of embodiment 1, wherein A02-A07 and B02-B07 comprise the sequence GGNNNN and N is any nucleotide, optionally wherein at least one of A02-A07 and B02-B07 comprise the sequence GGGGGC.

3. The polynucleotide of embodiment 1, wherein A02-A07 and B02-B07 comprise the sequence NNNNNN, which is a polynucleotide sequence present in the 3' UTR of an mRNA for an oncogene or a survival/housekeeping gene.

4. The polynucleotide of any of the above embodiments, wherein each of the A strand and the B strand down-regulates expression of one or more survival genes when the polynucleotide is transfected or expressed in a cell.

5. The polynucleotide of embodiment 1, wherein the contiguous sequence of A02-A07 and B02-B07 are independently selected from the group consisting of GGGCAG, GGGGCU, GGGCUG, GGGCGA, GGGCGC, GGGGCU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGC, GGCAUC, GCUGCU, CGGUGG, GUGUUC, GUCCAC, GGGCUU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, GGCUC, UCGUGC, GUUCCU, and GUCUGU.

6. The polynucleotide of any of the above embodiments, wherein at least one of the A strand and the B strand further comprises a 3' overhang comprising deoxyribonucleotides, optionally wherein the 3' overhang comprises dAdA or TT.
7. The polynucleotide of any of the above embodiments, wherein the polynucleotide is an siRNA.
8. The polynucleotide of any of embodiments 1-6, wherein the polynucleotide is an shRNA.
9. An expression vector that expresses the polynucleotide of any of the above embodiments.
10. A eukaryotic cell comprising the expression vector of embodiment 9, wherein the cell has been engineered to be deficient in a gene that is required for processing toxic RNA for RNA interference (RNAi).
11. An eleventh embodiment, including a polynucleotide comprising a dsRNA sequence having a first strand, otherwise referred to as an "A" strand, and a second strand, otherwise referred to as a "B" strand the dsRNA defined as follows:

```
5'-A01 A02 A03 A04 A05 A06 A07 A08 A09 A10 A11 A12 A13 A14 A15 A16 A17 A18 A19 A20 A21-3'
    |   |   |   |   |   |   |   |   |   |   |   |   |   |   |   |   |   |   |   |   |
3'-B21 B20 B19 B18 B17 B16 B15 B14 B13 B12 B11 B10 B09 B08 B07 B06 B05 B04 B03 B02 B01-5'
``` wherein:
A01 through A21 and B01 through B21 are any ribonucleotide selected from A, U, G, and C, provided that:
A01-A21 are complementary to B01-B21, respectively;
A01 and B01 are A or U;
the percentage GC content of the region in the A strand from A02-A07 is 66-100%, and the B strand comprises a trinucleotide repeat sequence $(X_1X_2X_3)_n$, wherein $X_1$, $X_2$, and $X_3$ independently are selected from any ribonucleotide A, C, G, and U, and n is an integer from 3-10; or the percentage GC content of the region in the B strand from B02-B07 is 66-100%, and the A strand comprises a trinucleotide repeat sequence $(X_1X_2X_3)_n$, wherein $X_1$, $X_2$, and $X_3$ independently are selected from any ribonucleotide A, C, G, and U, and n is an integer from 3-10.
12. The polynucleotide of embodiment 11, wherein A02-A07 or B02-B07 comprise the sequence GGNNNN and N is any nucleotide, optionally wherein at least one of A02-A07 and B02-B07 comprise the sequence GGGGGC.
13. The polynucleotide of embodiment 11, wherein A02-A07 or B02-B07 comprise the sequence NNNNNN, which is a polynucleotide sequence present in the 3' UTR of an mRNA for an oncogene or a survival/housekeeping gene.
14. The polynucleotide of any one of embodiments 11-13, wherein each of the A strand and the B strand downregulates expression of one or more survival genes when the polynucleotide is transfected or expressed in a cell.
15. The polynucleotide of embodiment 11, wherein the contiguous sequence of A02-A07 or B02-B07 is selected from the group consisting of GGGCAG, GGGGCU, GGGCUG, GGGCGA, GGGGGC, GGGGGU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, CGUGGG, GUAGGC, GCUGGG, GUCUCC, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGC, GGCAUC, GCUGCU, CGGUGG, GUGUUC, GUCCAC, GGGCUU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, CGGCUC, UCGUGC, GUUCCU, and GUCUGU.
16. The polynucleotide of any one of embodiments 11-15, wherein the trinucleotide repeat sequence has a GC content of at least 33%.
17. The polynucleotide of any one of embodiments 11-15, wherein the trinucleotide repeat sequence has a GC content of at least 66%.
18. The polynucleotide of any one of embodiments 11-17, wherein the trinucleotide repeat sequence is selected from the group consisting of $(ACC)_n$, $(ACG)_n$, $(AGC)_n$, $(AGG)_n$, $(CAC)_n$, $(CAG)_n$, $(CCA)_n$, $(CCC)_n$, $(CCG)_n$, $(CCU)_n$, $(CGA)_n$, $(CGC)_n$, $(CGG)_n$, $(CGU)_n$, $(CUC)_n$, (CUG)$_n$, (GAC)$_n$, (GAG)$_n$, (GCA)$_n$, (GCC)$_n$, (GCG)$_n$, (GCU)$_n$, (GGA)$_n$, (GGC)$_n$, (GGG)$_n$, (GGU)$_n$, (GUC)$_n$, (GUG)$_n$, (UCC)$_n$, (UCG)$_n$, (UGC)$_n$, and (UGG)$_n$.

19. The polynucleotide of any one of embodiments 11-18, wherein the trinucleotide repeat sequence is CAG or CUG.
20. The polynucleotide of any one of embodiment 11-19, wherein at least one of the A strand and the B strand further comprises a 3' overhang comprising deoxyribonucleotides, optionally wherein the 3' overhang comprises dAdA or TT.
21. The polynucleotide of any one of embodiments 11-20, wherein the polynucleotide is an siRNA.
22. The polynucleotide of any one of embodiments 11-20, wherein the polynucleotide is an shRNA.
23. An expression vector that expresses the polynucleotide of any one of the embodiments of 11-22.
24. A eukaryotic cell comprising the expression vector of embodiment 9 or 22, wherein the cell has been engineered to be deficient in a gene that is required for processing toxic RNA for RNA interference (RNAi).
25. A pharmaceutical composition comprising the polynucleotide of any of embodiments 1-8 or 11-22 or the expression vector of embodiments 9 or 23 and a pharmaceutically acceptable carrier, excipient, or diluent.
26. Extracellular vesicles comprising the polynucleotide of any of embodiments 1-8 or 11-22, optionally wherein the extracellular vesicles are exosomes.
27. A pharmaceutical composition comprising the extracellular vesicles of embodiment 26 and a pharmaceutically acceptable carrier, excipient, or diluent.
28. A method for treating a disease or disorder in a subject in need thereof, the method comprising administering to the subject the pharmaceutical composition of embodiment 25 or 27.
29. The method of embodiment 28, wherein the disease or disorder is a cell proliferative disease or disorder such as cancer.
30. A method of inhibiting the growth of a cancer cell or killing a cancer cell, the method comprising introducing or expressing the polynucleotide of claim of any of embodiment 1-8 or 11-22 in the cancer cell, and/or the method comprising introducing the expression vector of embodiment 9 or 23 into the cell.

Examples

The following Examples are illustrative and are not intended to limit the scope of the claimed subject matter.

Background

RNA interference (RNAi) is a form of post-transcriptional regulation exerted by 19-21 nt long double stranded RNAs that negatively regulate gene expression at the mRNA level. RNAi-active guide RNAs can come from endogenous siRNAs and micro(mi)RNAs. For a miRNA, the RNAi pathway begins in the nucleus with transcription of a primary miRNA precursor (pri-miRNA) (1). Pri-miRNAs are first processed by the Drosha/DGCR8 microprocessor complex into pre-miRNAs (2), which are then exported from the nucleus to the cytoplasm by Exportin 5 (3). Once in the cytoplasm, Dicer processes them further (4, 5) and these mature dsRNA duplexes are then loaded into Argonaute (Ago) proteins to form the RNA-induced silencing complex (RISC) (6). The sense/passenger strand is ejected/degraded, while the guide strand remains associated with the RISC (7). Depending on the degree of complementarity between the guide strand and its target, the outcome of RNAi can either be target degradation—most often achieved by siRNAs with full complementarity to their target mRNA (8)—or miRNA-like cleavage-independent silencing, mediated by deadenylation/degradation or translational repression (9). The latter mechanism can be initiated with as little as six nucleotide base-pairing between a guide RNA's so-called seed sequence (positions 2 to 7) and fully complementary seed matches in the target RNA (10, 11). This seed-based targeting most often occurs in the 3'UTR of a target mRNA (12, 13).

A number of miRNAs function either as tumor suppressors or as oncogenes (14). Their cancer specific activities are usually explained by their identified targets, being oncogenes or tumor suppressors, respectively (14). Examples of targets of tumor-suppressive miRNAs are the oncogenes Bcl-2 for miR-15/16 (15) and c-Myc for miR-34a (16). While many miRNAs have been reported to have both tumor suppressive and oncogenic activities depending on the cancer context, examples for widely established tumor promoting miRNAs are miR-221/222, miR-21, miR-155, and members of the miR-17-92 cluster, or its paralogues miR-106b-25 and miR-106a-363 (17, 18). In contrast, two of the major tumor suppressive miRNA families are miR-15/16 and the p53 regulated miR-34a/c and miR-34b (19).

We recently discovered that many si- and shRNAs can kill all tested cancer cell lines through RNAi by targeting the 3'UTRs of critical survival genes (20). We demonstrated that siRNA killed the cells through RNAi by showing that knockdown of AGO2 severely blunted the toxicity induced by either si- or shRNAs (20). In addition, toxic shRNAs were not toxic anymore when introduce into cells lacking Dicer expression as Dicer is required for processing of shRNAs (20).

We called this cell death mechanism DISE (for death induced by survival gene elimination). Cancer cells have difficulty developing resistance to this mechanism both in vitro and when treated in vivo (21). We reported that a 6mer seed sequence in the toxic siRNAs is sufficient for effective killing (20). We recently performed a strand specific siRNA screen with a library of individual siRNAs representing all 4096 possible 6mer seed sequences in a neutral RNA duplex. This screen, while based on siRNA biochemistry was not designed to identify targets that are degraded through siRNA mediated slicing activity but to identify toxicity caused by moderately targeting hundreds of genes required for cell survival in a mechanism similar to miRNA-induced silencing.

We found that the most toxic 6mer seeds are G-rich with a G enrichment towards the 5' end targeting survival genes with a high C content in their 3'UTR in a miRNA-like manner. The top 200 most toxic seeds had the consensus GGGGGC (22). Many tumor suppressive miRNAs such as miR-34a-5p but none of the established oncogenic miRNAs contain G-rich 6mer seeds and most of miR-34a-5p's toxicity comes from its 6mer seed sequence. Consistently, we demonstrate that for most miRNAs the more abundant mature form corresponds to the arm that contains the less toxic seed. In contrast, for major tumor suppressive miRNAs, the mature miRNA is derived from the arm that harbors the more toxic seed.

We found that normal cells are quite efficiently protected from this form of cell death by the expression of large amounts of RISC bound miRNAs that carry nontoxic seeds (20, 23, 24) (they have to, otherwise normal cells most of which express large amounts of miRNAs would die).

When we discovered DISE and found evidence that it could be a fundamental anti-cancer mechanism developed during evolution, we wondered whether there could be patients with a disease in which this mechanism was hyperactive. We predicted that this would result in degeneration of certain tissues and these patients would be expected to have lower cancer incidence. In addition, the disease had to involve a RNA component, preferentially even an RNAi component. We found these criteria were met in a number of trinucleotide repeat (TNR) expansion diseases. One of the TNR diseases, Huntington's disease (HD), stood out. HD is caused by the expansion of a CAG repeat in the gene huntingtin (HTT) (reviewed in (25)). When the repeat expansion in HTT exceeds a certain tolerated length, patients suffer from loss of neurons in a specific part of the brain resulting in a debilitating terminal neurodegenerative disorder. Furthermore, four independent studies reported an inverse correlation between the repeat length and the incidence of multiple cancers in HD patients. Finally, the CAG repeats in the HTT gene have been shown to be processed to small RNA active siRNAs (discussed in (23, 25)). In summary, HD and many other TNR diseases met the criteria of having an overactive anti-cancer mechanism. But could the CAG repeat sequences present in these patients be used to treat cancer? To test this, we designed siRNA duplexes based on the CAG repeat (present in HD patients) and the complementary CUG repeat (expanded in muscular dystrophy type I patients). Remarkably, these siRNAs killed all tested human and mouse cancer cell lines at very low concentrations (as low as 10 pM (23)). They were therefore 100-1000 times more toxic than any DISE inducing siRNA we had tested. To determine whether there was something special about CAG or CUG repeats we performed another screen testing all possible 60 trinucleotide repeat-based siRNAs. The only ones that were toxic to all cells were all siRNAs based on CAG and the complementary CUG TNR (23). We then provided evidence that the repeat-based siRNAs kill cancer cells by targeting genes that are critical for cell survival and contain repeat sequences themselves that are complementary to the toxic TNR-based siRNAs. TNR-based siRNAs therefore kill cancer cells by targeting the CDS of certain survival genes in a mechanism that is different from the DISE mechanism described above.

We recently developed a model of how TNR expansion sequences embedded in the genome of higher organisms could be part of an anti-cancer mechanism that we can now use to develop a new form of cancer therapy (25).

In summary, we now have two different types of toxic small RNAs that kill cancer cells through RNAi: 1) si/sh/miRNAs that kill the cells through 6mer seed toxicity in a miRNA-like fashion by targeting the 3'UTR of hundreds of survival genes and 2) TNR based siRNAs that kill cells by targeting multiple survival genes through siRNA like-targeting of completely complementary repeat regions present in the ORF of the targeted genes.

The Problem

To use the toxic si/sh/miRNAs for treatment of cancer there are multiple ways of delivering the RNAs to the cancer cells. While in the case of chemically synthesized siRNAs one can control which strand will be loaded into the RISC through chemical modification of the passenger strand, when using shRNAs (either expressed in cells to package them into extracellular vesicles) or expressed from viruses, it will not be that easy to determine which of the two RNA strands will be RNAi active in the cancer cells. Even when the strand with the most toxic activity will be expressed in most cancer cells, one cannot exclude that treated cancer cells mutate and find a way to degrade the toxic arm and load the nontoxic strand into the RISC which would then protect them from DISE. This way treated cancer could achieve therapy resistance.

The Disclosed Technology that Addresses this Problem

To prevent cancer cells from selecting the less toxic RNA strand form a super toxic double stranded shRNA we have now designed and tested two types of dual activity siRNAs that can also be converted to shRNAs. The first design contains in each strand at the 5' end (positions 2-7) one super toxic G-rich 6mer seed that came out of the screen of all 4096 different 6mer seeds (22). We have extended its length to 21 nucleotides, the optimal length to convert sequences to a shRNA. Due to the imprecision of Dicer in cleaving a simple stem loop shRNA the location of the 6mer seed in each strand may be varied by one or two nucleotide positions. In addition to the dual 6mer seed siRNA we also designed a bifunctional siRNA that contains in one strand the most toxic 6mer seed consensus GGGGGC and on the other strand consists of mostly CAG repeats allowing this design to engage both killing mechanisms at the same time. Again cancer cells cannot become resistant to this design by loading a nontoxic strand into the RISC.

DESCRIPTION OF THE TECHNOLOGY

Figure 2:
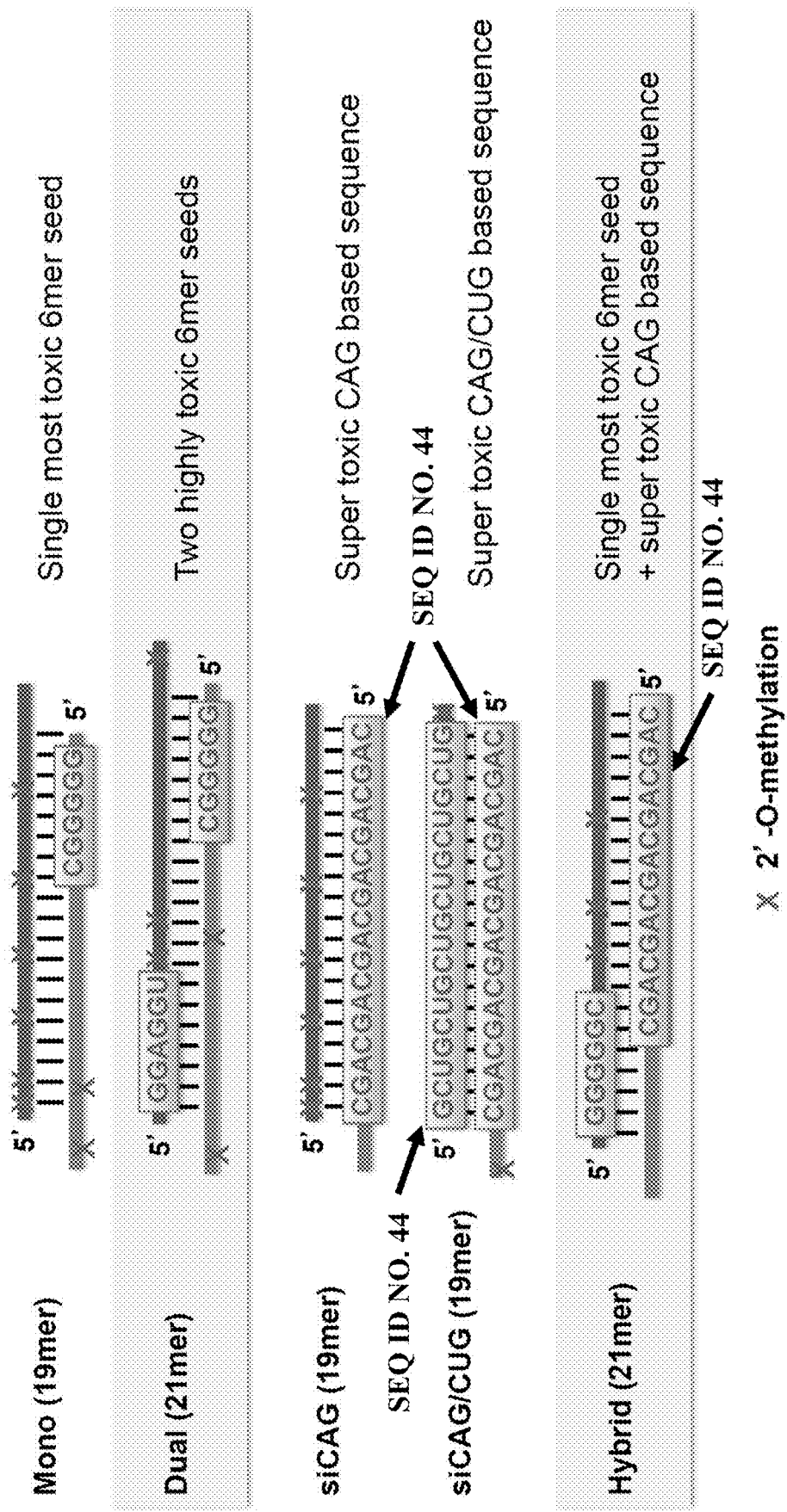
FIG. 2: Scheme displaying the different siRNA constructs. 2-O-methylation positions are shown as examples on how to stabilize each siRNA for in vivo use.

Based on our recent identification of 6mer seed toxicity and the rules underlying this toxicity (22) we had generated a most toxic seed containing siRNA that carries the toxic seed consensus GGGGGC (FIG. 1A) based on the 200 seeds most toxic two human cells (FIG. 1). This 6mer seed was indeed shown to be highly toxic when transfected into cells and when the 5' end of the passenger strand was blocked by 2'O-methylation in its first two positions. We demonstrated that this modification prevents passenger strand loading into the RISC (20, 23). It must be the goal of cancer therapy to design a drug that cancer cells cannot become resistant to and cannot evolve to find away around the cell death that is induced. We recently demonstrated that most miRNAs only express one of their two strands (3p or 5p arm) (22). For most miRNAs this is the arm that contains the 6mer seed predicted to be less toxic. An exception are a few tumor suppressive miRNAs. In these cases it is the arm predicted to have the higher toxicity that is expressed and the less toxic arm is degraded. The rules that govern this strand specific use and degradation are not fully understood. However, it is conceivable that cancer cells could become resistant to a toxic siRNA based on most miRNAs by switching to using the nontoxic arm and degrading the toxic arm. We therefore have developed two classes of dual activity si-/shRNAs that will be toxic regardless of what arm cancer cells degrade. We have designed two new super toxic bifunctional siRNAs (FIG. 2): in the first design we placed two super toxic 6mer seeds at the 5' end of each of the two strands, this could be any of the 200 seeds listed in FIG. 2B, however, we designed it by adding the most toxic consensus sequence GGGGGC on one end and the second most toxic seed GGAGGU (see https://6merdb.org) at the other. The two seeds could be any of the toxic seeds listed in FIG. 1B. To reduce the over all G content which could impair loading into the RISC more difficult, we extended the backbone of the siRNA by 2 nucleotides and designed the spacer in between the two opposite seeds to be AU rich (see FIG. 3A). In addition to the 6mer seed toxicity we also identified another mechanism to kill cancer cells based on TNR sequences. In the highly unlikely event that cancer cells become resistant to the 6mer seed toxicity we therefore designed a hybrid siRNA comprised of one strand carrying the GGGGGC consensus as a seed and on the other strand an extended CAG repeat (5 repeats) (FIG. 2). In theory this construct should be able to kill cancer cells through two powerful mechanisms and at the same time would again not allow cancer cells to become resistant to cell death by selectively degrading the more toxic strand.

Figure 3:
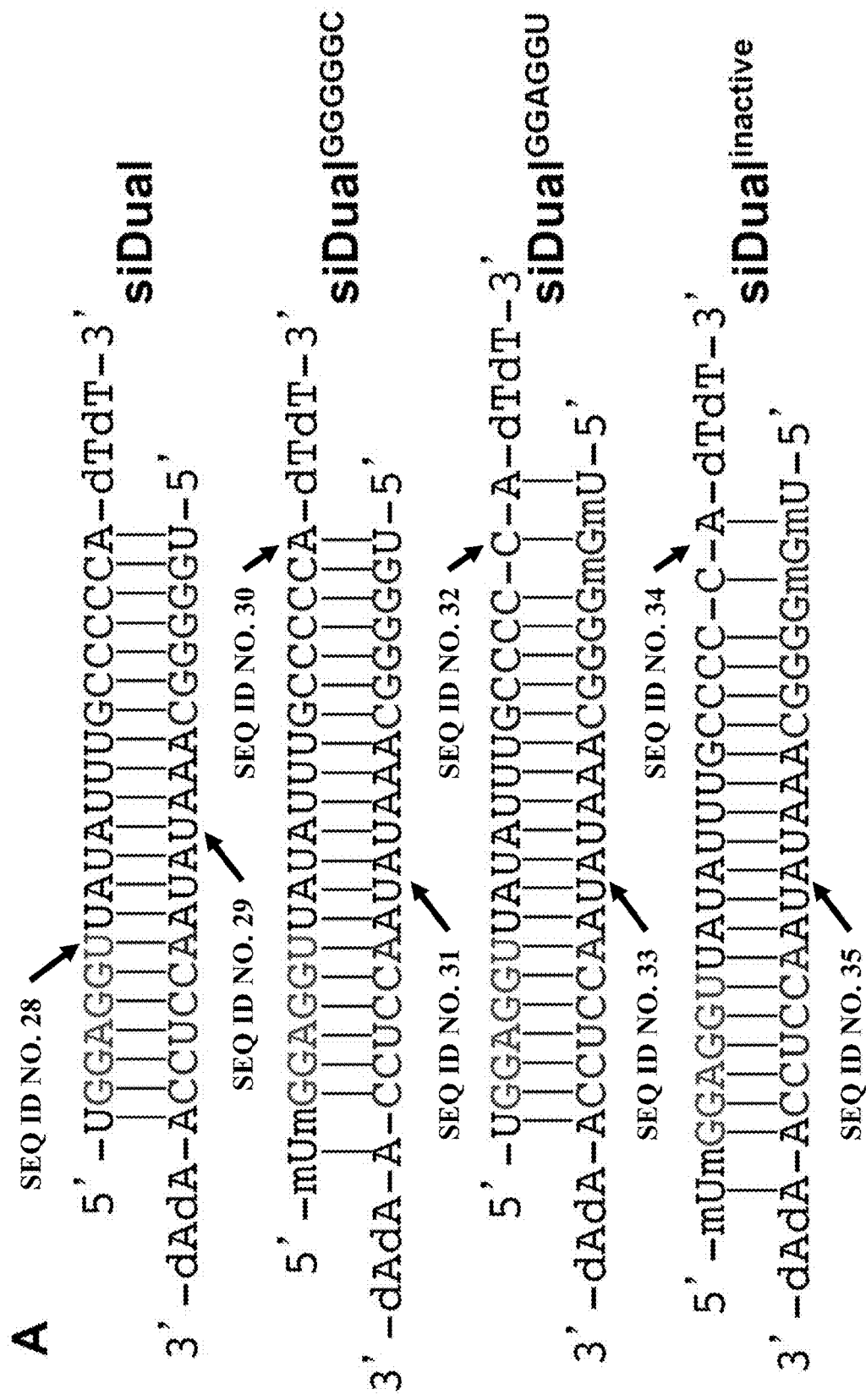
FIG. 3: Activity of the dual seed siRNA on HeyA8 cells with both strands active or one inactivated by OMe. (A) Sequences and 2-O-methylation positions of the different Dual activity siRNAs. (B) Change in confluency over time of HeyA8 cells transfected with 10 nM of the indicated siRNAs.
Figure 3:
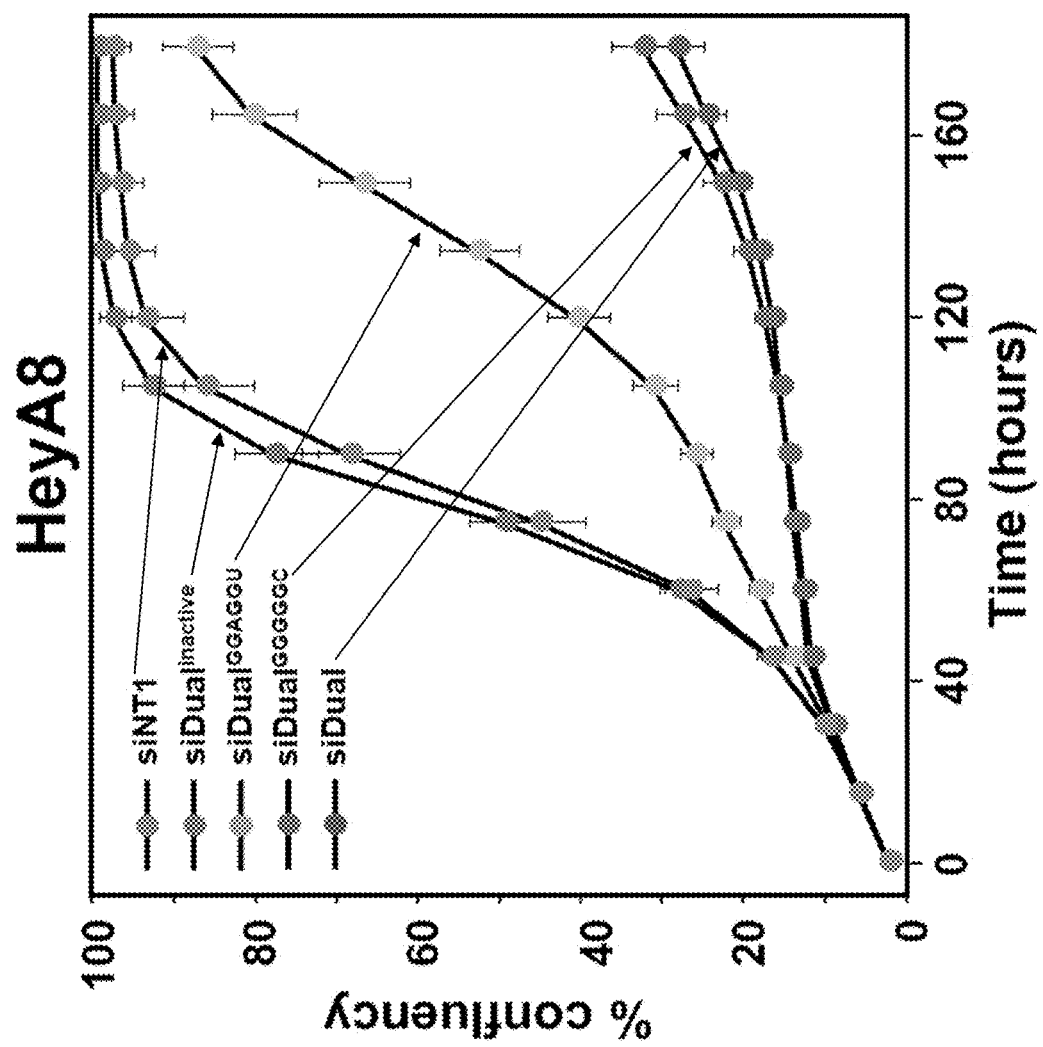
Figure 4:
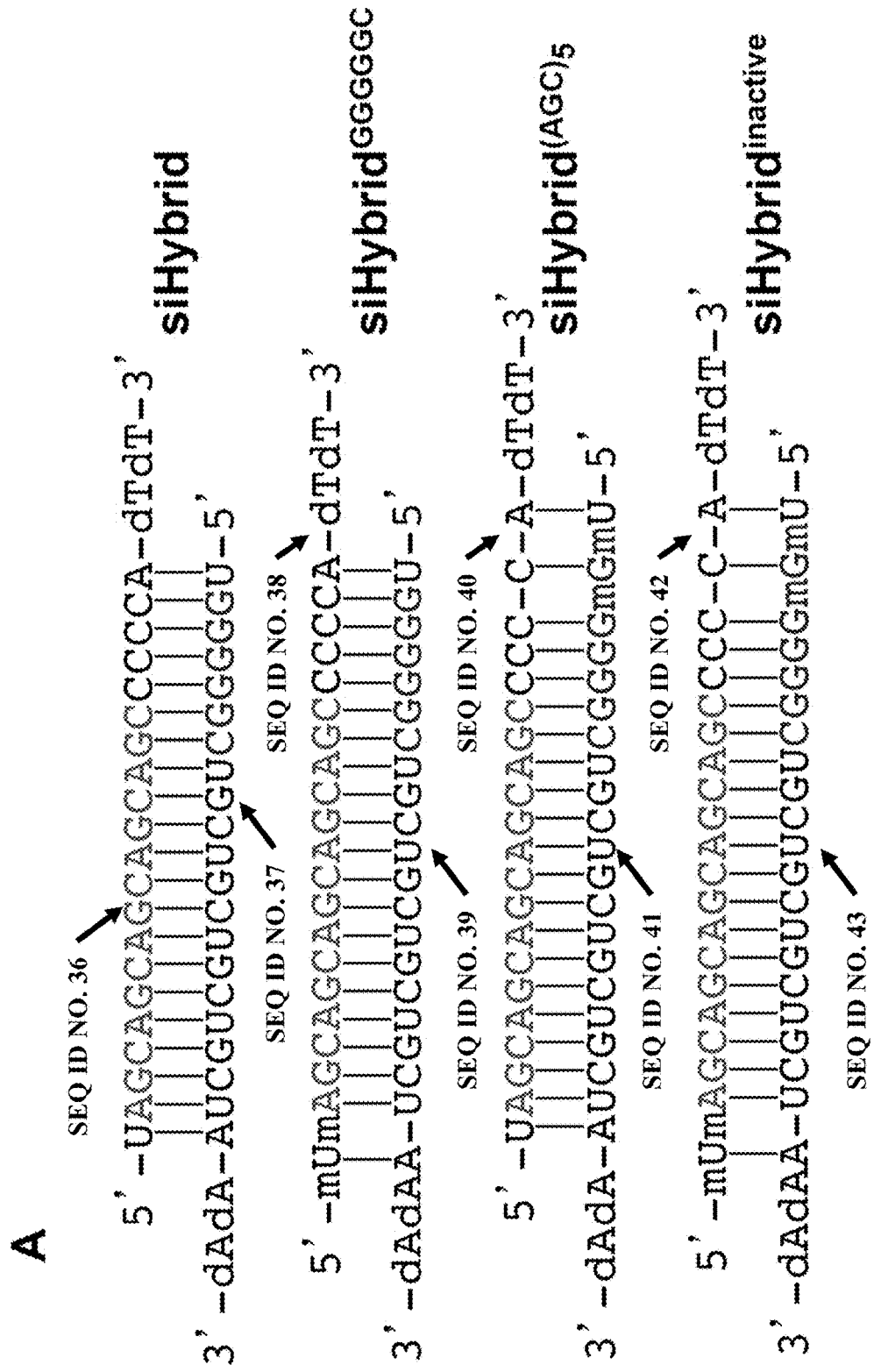
FIG. 4: Activity of the seed/CAG TNR siRNA hybrid on HeyA8 cells with both strands active or one inactivated by OMe. (A) Sequences and 2-O-methylation positions of the different hybrid siRNAs. (B) Change in confluency over time of HeyA8 cells transfected with 10 nM of the indicated siRNAs.
Figure 4:
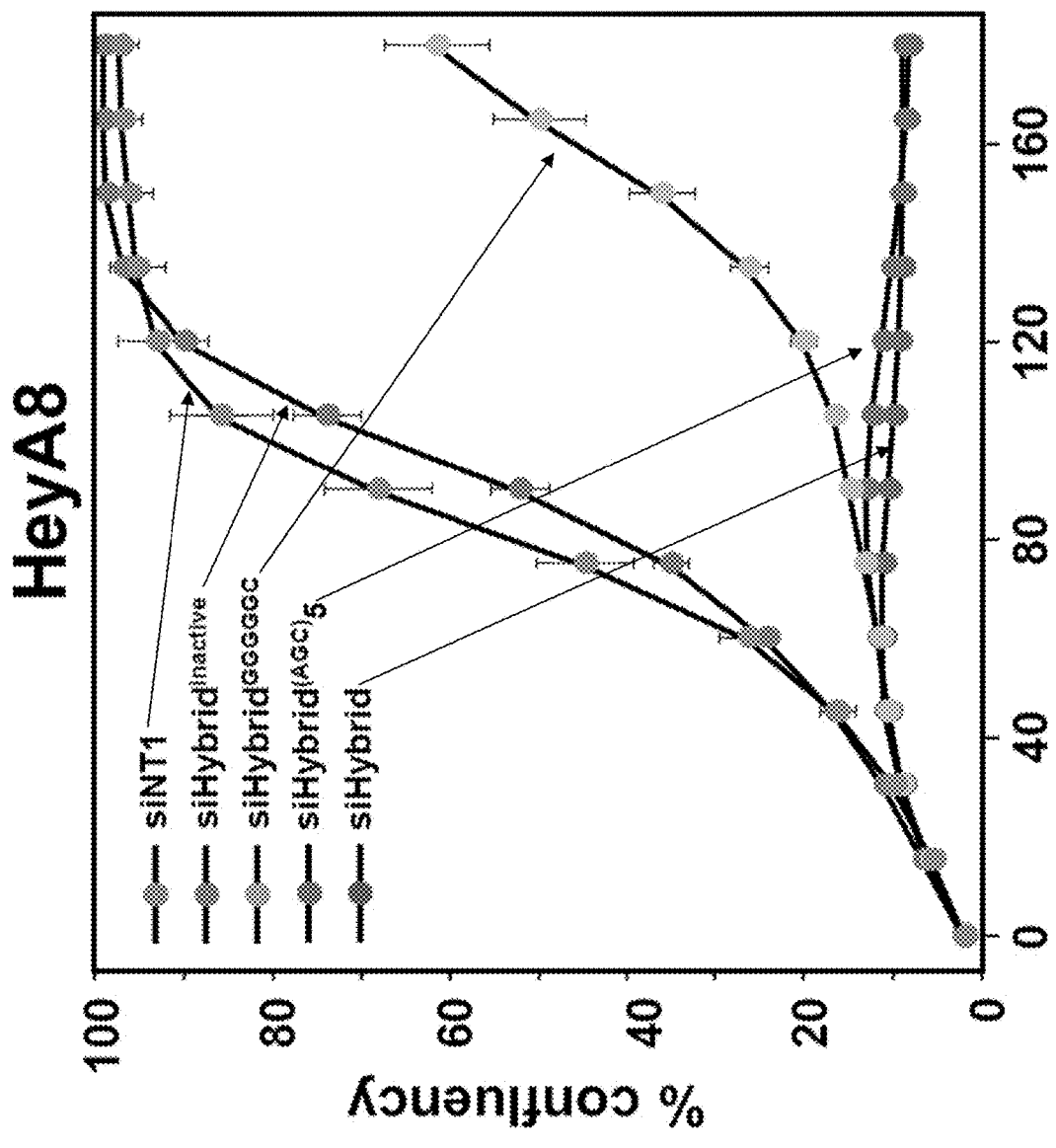

We first tested the dual activity (double seed) siRNA (FIG. 3). By modifying 5' end with O-methylations (FIG. 3A) we tested the activity of this siRNA when one or both strands were inactivated (FIG. 3B). As expected the unmodified siRNA was most toxic to the cells. Most of this toxicity came from the strand carrying the GGGGGC consensus but when this strand was inactivated the siRNA was still toxic through the seed on its other strand (GGAGGU). No toxicity was observed when both strands were inactivated.

A similar result was seen when the hybrid siRNA was tested. Most of the toxicity of this siRNA came from its CAG based repeat that was still fully active despite the presence of the 6mer seed on the other strand (which overlaps by two nucleotide with the end of the CAG repeat). Likely due to the overall GC rich sequence of the siRNA duplex the GGGGGC strand alone after inactivating the CAG repeat strand was less toxic than in the dual seed siRNA (see FIG. 3), however, it was still toxic to the cells suggesting that this hybrid siRNA can indeed kill cancer cells simultaneously through the two different RNAi based mechanisms we described and even in the unlikely event that cancer cells could become resistant to triggering one of the two kill codes they could still die through the other mechanism.

This invention can be used for both siRNAs and more importantly when designing shRNAs either for loading cells to produce extracellular vesicles of for designing toxic viruses.

REFERENCES

1. Lee Y, Kim M, Han J, Yeom K H, Lee S, Baek S H, Kim V N. (2004). MicroRNA genes are transcribed by RNA polymerase I I. EMBO J. 23:4051-60.
2. Han J, Lee Y, Yeom K H, Kim Y K, Jin H, Kim V N. (2004). The Drosha-DGCR8 complex in primary microRNA processing. Genes Dev. 18:3016-27.
3. Yi R, Qin Y, Macara I G, Cullen B R. (2003). Exportin-5 mediates the nuclear export of pre-microRNAs and short hairpin RNAs. Genes Dev. 17:3011-6.
4. Bernstein E, Caudy A A, Hammond S M, Hannon G J. (2001). Role for a bidentate ribonuclease in the initiation step of RNA interference. Nature. 409:363-6.
5. Hutvagner G, McLachlan J, Pasquinelli A E, Balint E, Tuschl T, Zamore P D. (2001). A cellular function for the RNA-interference enzyme Dicer in the maturation of the let-7 small temporal RNA. Science. 293:834-8.
6. Wang Y, Sheng G, Juranek S, Tuschl T, Patel D J. (2008). Structure of the guide-strand-containing argonaute silencing complex. Nature. 456:209-13.
7. Leuschner P J, Ameres S L, Kueng S, Martinez J. (2006). Cleavage of the siRNA passenger strand during RISC assembly in human cells. EMBO Rep. 7:314-20.
8. Schirle N T, MacRae I J. (2012). The crystal structure of human Argonaute2. Science. 336:1037-40.
9. Eulalio A, Huntzinger E, Izaurralde E. (2008). GW182 interaction with Argonaute is essential for miRNA-mediated translational repression and mRNA decay. Nat Struct Mol Biol. 15:346-53.
10. Lewis B P, Shih I H, Jones-Rhoades M W, Bartel D P, Burge C B. (2003). Prediction of mammalian microRNA targets. Cell. 115:787-98.
11. Lai E C. (2002). Micro RNAs are complementary to 3' UTR sequence motifs that mediate negative post-transcriptional regulation. Nat Genet. 30:363-4.
12. Selbach M, Schwanhausser B, Thierfelder N, Fang Z, Khanin R, Rajewsky N. (2008). Widespread changes in protein synthesis induced by microRNAs. Nature. 455: 58-63.
13. Baek D, Villen J, Shin C, Camargo F D, Gygi S P, Bartel D P. (2008). The impact of microRNAs on protein output. Nature. 455:64-71.
14. Esquela-Kerscher A, Slack F J. (2006). Oncomirs—microRNAs with a role in cancer. Nat Rev Cancer. 6:259-69.
15. Balatti V, Pekarky Y, Rizzotto L, Croce C M. (2013). miR deregulation in CLL. Adv Exp Med Biol. 792:309-25.
16. Slabakova E, Culig Z, Remsik J, Soucek K. (2017). Alternative mechanisms of miR-34a regulation in cancer. Cell Death Dis. 8:e3100.
17. Hua Y J, Larsen N, Kalyana-Sundaram S, Kjems J, Chinnaiyan A M, Peter M E. (2013). miRConnect 2.0: Identification of antagonistic, oncogenic miRNA families in three human cancers. BMC Genomics. 14:179.
18. Concepcion C P, Bonetti C, Ventura A. (2012). The microRNA-17-92 family of microRNA clusters in development and disease. Cancer journal. 18:262-7.
19. He X, He L, Hannon G J. (2007). The guardian's little helper: microRNAs in the p53 tumor suppressor network. Cancer Res. 67:11099-101.
20. Putzbach W, Gao Q Q, Patel M, van Dongen S, Haluck-Kangas A, Sarshad A A, Bartom E, Kim K Y, Scholtens D M, Hafner M, Zhao J C, Murmann A E, Peter M E. (2017). Many si/shRNAs can kill cancer cells by targeting multiple survival genes through an off-target mechanism. eLife. 6: e29702.
21. Murmann A E, McMahon K M, Halluck-Kangas A, Ravindran N, Patel M, Law C, Brockway S, Wei J J, Thaxton C S, Peter M E. (2017). Induction of DISE in ovarian cancer cells in vivo. Oncotarget. 8:84643-58.
22. Gao Q Q, Putzbach W, Murmann A E, Chen S, Ambrosini G, Peter J M, Bartom E, Peter M E. (2018). 6mer seed toxicity in tumor suppressive miRNAs. Nature Comm. 9:4504.
23. Murmann A E, Gao Q Q, Putzbach W T, Patel M, Bartom E T, Law C Y, Bridgeman B, Chen S, McMahon K M, Thaxton C S, Peter M E. (2018). Small interfering RNAs based on huntingtin trinucleotide repeats are highly toxic to cancer cells. EMBO Rep. 19:e45336.
24. Putzbach W, Gao Q Q, Patel M, Haluck-Kangas A, Murmann A E, Peter M E. (2018). DISE—A Seed Dependent RNAi Off-Target Effect that Kills Cancer Cells. Trends in Cancer. 4:10-9.
25. Murmann A E, Yu J, Opal P, Peter M E. (2018). Trinucleotide repeat expansion diseases, RNAi and cancer. Trends in Cancer. 4:684-700.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. An shRNA polynucleotide comprising a dsRNA sequence having a first strand, otherwise referred to as an "A" strand, and a second strand, otherwise referred to as a "B" strand, the dsRNA defined as follows:

```
5'-A01 A02 A03 A04 A05 A06 A07 A08 A09 A10 A11 A12
    |   |   |   |   |   |   |   |   |   |   |   |
3'-B21 B20 B19 B18 B17 B16 B15 B14 B13 B12 B11 B10

A13 A14 A15 A16 A17 A18 A19 A20 A21-3'
        |   |   |   |   |   |   |   |   |
       B09 B08 B07 B06 B05 B04 B03 B02 B01-5'
``` wherein:
A01 through A21 and B01 through B21 are any ribonucleotide selected from A, U, G, and C, provided that:
(i) A01-A21 are complementary to B01-B21, respectively;
(ii) A01 and B01 are A or U;
(iii) one of the A strand from A02-A07 and the B strand from B02-B07 comprises the sequence GGGGGC; and
(iv) the other of the A strand and the B strand comprises a trinucleotide repeat sequence (CAG)$_n$, wherein n is an integer from 3-10;

wherein the 3' end of the A strand is linked via polynucleotides to the 5' end of the B strand; and wherein both of the A strand and the B strand are toxic after the shRNA is introduced into a cell and the shRNA is processed for RNA interference, wherein the dsRNA sequence comprises:

(SEQ ID NOs: 47 and 48)
```
5'-CAGCAGCAGCAGCCCCC-3'
   |||||||||||||||||
3'-GUCGUCGUCGUCGGGGG-5'.
```

2. A pharmaceutical composition comprising the shRNA polynucleotide of claim 1 and a pharmaceutically acceptable carrier, excipient, or diluent.

* * * * *

SEQUENCE LISTING

```
<160> NUMBER OF SEQ ID NOS: 48

<210> SEQ ID NO 1
<211> LENGTH: 19
<212> TYPE: RNA
<213> ORGANISM: Artificial
<220> FEATURE:
<223> OTHER INFORMATION: Artificial siRNA designed to include a seed
      sequence that is non-targeting in mammalian cells

<400> SEQUENCE: 1
ugguuuacau guguguga                                                    19

<210> SEQ ID NO 2
<211> LENGTH: 19
<212> TYPE: RNA
<213> ORGANISM: Artificial
<220> FEATURE:
<223> OTHER INFORMATION: Artificial siRNA designed to include a seed
      sequence that is non-targeting in mammalian cells

<400> SEQUENCE: 2
ugguuuacau gucgacuaa                                                   19

<210> SEQ ID NO 3
<211> LENGTH: 19
<212> TYPE: RNA
<213> ORGANISM: Homo sapiens

<400> SEQUENCE: 3
gcccuucaau uacccauau                                                   19

<210> SEQ ID NO 4
<211> LENGTH: 19
<212> TYPE: RNA
<213> ORGANISM: Artificial
<220> FEATURE:
<223> OTHER INFORMATION: Artificial siRNA designed to include seed
      sequence for human CD95L exon 1

<400> SEQUENCE: 4
ugguuuacau gucccauaa                                                   19

<210> SEQ ID NO 5
<211> LENGTH: 19
<212> TYPE: RNA
<213> ORGANISM: Artificial
<220> FEATURE:
<223> OTHER INFORMATION: Artificial siRNA designed to include a seed
      sequence that is non-targeting in mammalian cells

<400> SEQUENCE: 5
ugguaaacua guugucuga                                                   19
```

```
<210> SEQ ID NO 6
<211> LENGTH: 19
<212> TYPE: RNA
<213> ORGANISM: Artificial
<220> FEATURE:
<223> OTHER INFORMATION: Artificial siRNA designed to include seed
      sequence for human CD95L exon 1

<400> SEQUENCE: 6
ugguaaacua gucccauaa                                                  19

<210> SEQ ID NO 7
<211> LENGTH: 21
<212> TYPE: DNA
<213> ORGANISM: Artificial
<220> FEATURE:
<223> OTHER INFORMATION: Artificial siRNA designed to include CAG
      triplet repeat and terminal dideoxynucleotide adenines

<400> SEQUENCE: 7
cagcagcagc agcagcagca a                                               21

<210> SEQ ID NO 8
<211> LENGTH: 21
<212> TYPE: DNA
<213> ORGANISM: Artificial
<220> FEATURE:
<223> OTHER INFORMATION: Artificial siRNA designed to include antisense
      sequence for siRNA containing CAG repeats and include
      dideoxynucleotide thymidines

<400> SEQUENCE: 8
gcugcugcug cugcugcugt t                                               21

<210> SEQ ID NO 9
<211> LENGTH: 10
<212> TYPE: DNA
<213> ORGANISM: Homo sapien

<400> SEQUENCE: 9
ctgctgctgc                                                            10

<210> SEQ ID NO 10
<211> LENGTH: 10
<212> TYPE: DNA
<213> ORGANISM: Homo sapien

<400> SEQUENCE: 10
tctgagacca                                                            10

<210> SEQ ID NO 11
<211> LENGTH: 10
<212> TYPE: DNA
<213> ORGANISM: Homo sapien

<400> SEQUENCE: 11
tgctgctgct                                                            10

<210> SEQ ID NO 12
<211> LENGTH: 10
<212> TYPE: DNA
<213> ORGANISM: Homo sapien

<400> SEQUENCE: 12
``` ggggtgggg                                                                10

<210> SEQ ID NO 13
<211> LENGTH: 10
<212> TYPE: DNA
<213> ORGANISM: Homo sapien

<400> SEQUENCE: 13
cctccctccc                                                                10

<210> SEQ ID NO 14
<211> LENGTH: 10
<212> TYPE: DNA
<213> ORGANISM: Homo sapien

<400> SEQUENCE: 14
ccccgccccc                                                                10

<210> SEQ ID NO 15
<211> LENGTH: 10
<212> TYPE: DNA
<213> ORGANISM: Homo sapien

<400> SEQUENCE: 15
ggccctggcc                                                                10

<210> SEQ ID NO 16
<211> LENGTH: 10
<212> TYPE: DNA
<213> ORGANISM: Homo sapien

<400> SEQUENCE: 16
cactccccac                                                                10

<210> SEQ ID NO 17
<211> LENGTH: 10
<212> TYPE: DNA
<213> ORGANISM: Homo sapien

<400> SEQUENCE: 17
ggcaggggtg                                                                10

<210> SEQ ID NO 18
<211> LENGTH: 10
<212> TYPE: DNA
<213> ORGANISM: Homo sapien

<400> SEQUENCE: 18
gggggtgggg                                                                10

<210> SEQ ID NO 19
<211> LENGTH: 10
<212> TYPE: DNA
<213> ORGANISM: Homo sapien

<400> SEQUENCE: 19
cctccctccc                                                                10

<210> SEQ ID NO 20
<211> LENGTH: 10
<212> TYPE: DNA
<213> ORGANISM: Homo sapien

<400> SEQUENCE: 20
ccccgccccc                                                                      10

<210> SEQ ID NO 21
<211> LENGTH: 19
<212> TYPE: DNA
<213> ORGANISM: Homo sapien

<400> SEQUENCE: 21
gctgctgctg ctgctgctg                                                            19

<210> SEQ ID NO 22
<211> LENGTH: 21
<212> TYPE: DNA
<213> ORGANISM: Artificial
<220> FEATURE:
<223> OTHER INFORMATION: Artificial siRNA designed to include CAG
      triplet repeat and terminal dideoxynucleotide adenines

<400> SEQUENCE: 22
agcagcagca gcagcagcaa a                                                         21

<210> SEQ ID NO 23
<211> LENGTH: 21
<212> TYPE: DNA
<213> ORGANISM: Artificial
<220> FEATURE:
<223> OTHER INFORMATION: Artificial siRNA designed to include antisense
      sequence for siRNA containing CAG repeats and include
      dideoxynucleotide thymidines

<400> SEQUENCE: 23
ugcugcugcu gcugcugcut t                                                         21

<210> SEQ ID NO 24
<211> LENGTH: 21
<212> TYPE: DNA
<213> ORGANISM: Artificial
<220> FEATURE:
<223> OTHER INFORMATION: Artificial siRNA designed to include CAG
      triplet repeat and terminal dideoxynucleotide adenines

<400> SEQUENCE: 24
gcagcagcag cagcagcaga a                                                         21

<210> SEQ ID NO 25
<211> LENGTH: 21
<212> TYPE: DNA
<213> ORGANISM: Artificial
<220> FEATURE:
<223> OTHER INFORMATION: Artificial siRNA designed to include antisense
      sequence for siRNA containing CAG repeats and include
      dideoxynucleotide thymidines

<400> SEQUENCE: 25
cugcugcugc ugcugcugct t                                                         21

<210> SEQ ID NO 26
<211> LENGTH: 21
<212> TYPE: DNA
<213> ORGANISM: Artificial
<220> FEATURE:
<223> OTHER INFORMATION: Artificial non-toxic scaffold sequence for
      guide strand of artificial siRNA including dideoxynucleotide
      adenines
<220> FEATURE:
<221> NAME/KEY: misc_feature
<222> LOCATION: (2)..(7)

<223> OTHER INFORMATION: n is a, c, g, t or u

<400> SEQUENCE: 26
unnnnnnaca uguaaagcca a                                              21

<210> SEQ ID NO 27
<211> LENGTH: 21
<212> TYPE: DNA
<213> ORGANISM: Artificial
<220> FEATURE:
<223> OTHER INFORMATION: Artificial non-toxic scaffold sequence for
      passenger strand of artificial siRNA including dideoxynucleotide
      thymidines
<220> FEATURE:
<221> NAME/KEY: misc_feature
<222> LOCATION: (13)..(18)
<223> OTHER INFORMATION: n is a, c, g, t or u

<400> SEQUENCE: 27
cgguuuacau gunnnnnnat t                                              21

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
uggagguuau auuugccccc att                                            23

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29 uggggggcaaa uauaaccucc aaa                                           23

<210> SEQ ID NO 30
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(2)
<223> OTHER INFORMATION: O-methylation

<400> SEQUENCE: 30
uggagguuau auuugccccc att                                            23

<210> SEQ ID NO 31
<211> LENGTH: 23
<212> TYPE: DNA
<213> ORGANISM: Artificial Sequence
<220> FEATURE:
<223> OTHER INFORMATION: Synthetic

<400> SEQUENCE: 31 uggggggcaaa uauaaccucc aaa                                           23

<210> SEQ ID NO 32
<211> LENGTH: 22

-continued

<212> TYPE: DNA
<213> ORGANISM: Artificial Sequence
<220> FEATURE:
<223> OTHER INFORMATION: Synthetic

<400> SEQUENCE: 32
uggagguuau auugcccca tt                                              22

<210> SEQ ID NO 33
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (2)..(3)
<223> OTHER INFORMATION: O-methylation

<400> SEQUENCE: 33 uggggggcaaa uauaaccucc aaa                                           23

<210> SEQ ID NO 34
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(2)
<223> OTHER INFORMATION: O-methylation

<400> SEQUENCE: 34
uggagguuau auugccccc att                                             23

<210> SEQ ID NO 35
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (2)..(3)
<223> OTHER INFORMATION: O-methylation

<400> SEQUENCE: 35 uggggggcaaa uauaaccucc aaa                                           23

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
uagcagcagc agcagccccc att                                            23

<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37

```
uggggggcugc ugcugcugcu aaa                                    23
```

\<210\> SEQ ID NO 38
\<211\> LENGTH: 23
\<212\> TYPE: DNA
\<213\> ORGANISM: Artificial Sequence
\<220\> FEATURE:
\<223\> OTHER INFORMATION: Synthetic
\<220\> FEATURE:
\<221\> NAME/KEY: modified_base
\<222\> LOCATION: (1)..(2)
\<223\> OTHER INFORMATION: O-methylation

\<400\> SEQUENCE: 38

```
uagcagcagc agcagccccc att                                     23
```

\<210\> SEQ ID NO 39
\<211\> LENGTH: 23
\<212\> TYPE: DNA
\<213\> ORGANISM: Artificial Sequence
\<220\> FEATURE:
\<223\> OTHER INFORMATION: Synthetic

\<400\> SEQUENCE: 39

```
uggggggcugc ugcugcugcu aaa                                    23
```

\<210\> SEQ ID NO 40
\<211\> LENGTH: 23
\<212\> TYPE: DNA
\<213\> ORGANISM: Artificial Sequence
\<220\> FEATURE:
\<223\> OTHER INFORMATION: Synthetic

\<400\> SEQUENCE: 40

```
uagcagcagc agcagccccc att                                     23
```

\<210\> SEQ ID NO 41
\<211\> LENGTH: 23
\<212\> TYPE: DNA
\<213\> ORGANISM: Artificial Sequence
\<220\> FEATURE:
\<223\> OTHER INFORMATION: Synthetic
\<220\> FEATURE:
\<221\> NAME/KEY: modified_base
\<222\> LOCATION: (2)..(3)
\<223\> OTHER INFORMATION: O-methylation

\<400\> SEQUENCE: 41

```
uggggggcugc ugcugcugcu aaa                                    23
```

\<210\> SEQ ID NO 42
\<211\> LENGTH: 22
\<212\> TYPE: DNA
\<213\> ORGANISM: Artificial Sequence
\<220\> FEATURE:
\<223\> OTHER INFORMATION: Synthetic
\<220\> FEATURE:
\<221\> NAME/KEY: modified_base
\<222\> LOCATION: (1)..(2)
\<223\> OTHER INFORMATION: O-methylation

\<400\> SEQUENCE: 42

```
uagcagcagc agcagcccca tt                                      22
```

\<210\> SEQ ID NO 43
\<211\> LENGTH: 23
\<212\> TYPE: DNA
\<213\> ORGANISM: Artificial Sequence

```
<220> FEATURE:
<223> OTHER INFORMATION: Synthetic
<220> FEATURE:
<221> NAME/KEY: modified_base
<222> LOCATION: (2)..(3)
<223> OTHER INFORMATION: O-methylation

<400> SEQUENCE: 43 uggggggcugc ugcugcugcu aaa                                          23

<210> SEQ ID NO 44
<211> LENGTH: 19
<212> TYPE: DNA
<213> ORGANISM: Artificial Sequence
<220> FEATURE:
<223> OTHER INFORMATION: Synthetic

<400> SEQUENCE: 44
cagcagcagc agcagcagc                                                19

<210> SEQ ID NO 45
<211> LENGTH: 19
<212> TYPE: DNA
<213> ORGANISM: Artificial Sequence
<220> FEATURE:
<223> OTHER INFORMATION: Synthetic

<400> SEQUENCE: 45
gcugcugcug cugcugcug                                                19

<210> SEQ ID NO 46
<211> LENGTH: 16
<212> TYPE: DNA
<213> ORGANISM: Artificial Sequence
<220> FEATURE:
<223> OTHER INFORMATION: Synthetic

<400> SEQUENCE: 46
cagcagcagc agcagc                                                   16

<210> SEQ ID NO 47
<211> LENGTH: 17
<212> TYPE: RNA
<213> ORGANISM: Artificial Sequence
<220> FEATURE:
<223> OTHER INFORMATION: Synthetic

<400> SEQUENCE: 47
cagcagcagc agccccc                                                  17

<210> SEQ ID NO 48
<211> LENGTH: 17
<212> TYPE: RNA
<213> ORGANISM: Artificial Sequence
<220> FEATURE:
<223> OTHER INFORMATION: Synthetic

<400> SEQUENCE: 48
gggggcugcu gcugcug                                                  17
```